United States Patent
Yura et al.

(10) Patent No.: US 7,226,611 B2
(45) Date of Patent: Jun. 5, 2007

(54) GLYCOSAMINOGLYCAN/COLLAGEN COMPLEXES AND USE THEREOF

(75) Inventors: Hirofumi Yura, Kawasaki (JP); Masayuki Ishihara, Tachikawa (JP); Yoshio Saito, Yokohama (JP); Katsuaki Ono, Tokorozawa (JP); Masato Sato, Yokohama (JP)

(73) Assignee: Yaizu Suisankagaku Industry Co., Ltd., Shizuoka (JP)

( * ) Notice: Subject to any disclaimer, the term of this patent is extended or adjusted under 35 U.S.C. 154(b) by 332 days.

(21) Appl. No.: 10/472,347

(22) PCT Filed: Apr. 2, 2002

(86) PCT No.: PCT/JP02/03287

§ 371 (c)(1),
(2), (4) Date: Feb. 12, 2004

(87) PCT Pub. No.: WO02/081619

PCT Pub. Date: Oct. 17, 2002

(65) Prior Publication Data

US 2004/0141945 A1 Jul. 22, 2004

(30) Foreign Application Priority Data

Apr. 2, 2001 (JP) ............................. 2001-102883

(51) Int. Cl.
*A61F 2/02* (2006.01)
*C12M 3/00* (2006.01)
(52) U.S. Cl. .................... 424/423; 435/283.1; 435/395
(58) Field of Classification Search .................... None
See application file for complete search history.

(56) References Cited

U.S. PATENT DOCUMENTS

| 4,060,081 A | * | 11/1977 | Yannas et al. | ........... 623/15.12 |
| 4,280,954 A | * | 7/1981 | Yannas et al. | ............... 530/356 |
| 4,488,911 A | * | 12/1984 | Luck et al. | ............... 106/157.2 |
| 4,947,840 A | * | 8/1990 | Yannas et al. | ................. 602/50 |
| 5,128,134 A | * | 7/1992 | Fyodorov et al. | ............ 424/427 |
| 5,476,666 A | * | 12/1995 | Rhee et al. | .................. 424/484 |
| 5,658,582 A | * | 8/1997 | Dorigatti et al. | ............ 424/402 |
| 5,851,230 A | * | 12/1998 | Weadock et al. | ........... 623/1.47 |
| 7,005,513 B1 | * | 2/2006 | Yura et al. | ................... 536/55.1 |

FOREIGN PATENT DOCUMENTS

| JP | 3-198768 | 8/1991 |
| JP | 8-168372 | 7/1996 |
| WO | WO 93/05793 | 9/1993 |
| WO | WO 00/59967 | 10/2000 |

* cited by examiner

*Primary Examiner*—Robert A. Wax
(74) *Attorney, Agent, or Firm*—Pearne & Gordon LLP

(57) ABSTRACT

The present invention is intended to offer a novel material which combines cell-adhesive proteins such as collagen with GAG polymers to construct an environment similar to an extracellular matrix, capable of controlling differentiation and proliferation of cells. The present invention offers a glycosaminoglycan-functionalized polymer protein composite produced by combining a cell-adhesive protein with a glycosaminoglycan-functionalized polymer obtained by incorporating a carbohydrate chain containing a structure corresponding to at least a portion of a glycosaminoglycan backbone into a vinyl polymer main chain, as well as a cell culture substrate and a material for tissue reconstruction treatments comprising the composite.

7 Claims, 7 Drawing Sheets

GLYCOSAMINOGLYCAN/COLLAGEN COMPLEXES AND USE THEREOF

TECHNICAL FIELD

The present invention relates to composites obtainable by combining glycosaminoglycans with cell-adhesive proteins such as collagen. In particular, the invention relates to composite materials obtainable by combining vinyl polymers having a glycosaminoglycan structure with cell-adhesive proteins such as collagen characterized by enhancement of the function of controlling cell growth possessed by glycosaminoglycans, particularly an action of controlling cell proliferation and differentiation by binding with various types of cell growth factors or cytokines characteristic of heparin and heparan sulfate, and their application to medicine.

BACKGROUND ART

The acidic polysaccharides known as glycosaminoglycans (GAGs), including heparin/heparan sulfate (HS), chondroitin sulfate, dermatan sulfate, keratan sulfate and hyaluronic add, present in connective tissue and the cell membrane, aggregate around a core protein with covalent bond to form proteoglycans (PGs). PGs form extracellular matrices (ECMs) with cell-adhesive proteins such as fibronectin, vitronectin, laminin, collagen and thrombospondin, and are widely distributed for supporting cell survival and physiological functions of cells. In particular, heparan sulfate proteoglycans (HSPGs) are present in almost all animal tissues, and perform a crucial role in the processes of cell adhesion, morphogenesis and maintenance of function.

It has become apparent that the heparin/HS found in PGs interact with various cell growth factors to control cell differentiation and proliferation. For example, fibroblast growth factors (FGFS) which have a high affinity to heparin/HS constitutes the FGF family (FGF1–FGF10 have been reported to date), and act specifically with respect to vascular endothelial cells, Kaposi's sarcoma cells and epidermal keratinized cells depending on their type. The activities of FGFs are believed to be triggered by binding specifically to FGF receptors (FGFRS) on the cell surfaces. Heparin/HS, which is present transmembranously, holds and stores unstable FGF molecules in a stable state in the vicinity of the cell, and support binding of the FGFs to the FGFRs as needed while protecting the FGFs from proteases and oxidative decomposition. The binding of FGFs to FGFRs causes proliferation signals to be generated, thus accelerating cell proliferation. This action mechanism is suggested by a large number of studies indicating that FGFs and FGFRs cannot bind unless heparin/HS is present (e.g., M. Ishihara, *Glycobiology*, 4, 817–824, 1994).

On the other hand, chondroitin sulfate exists in abundance in the massive hyaluronic acid-rich PG backbones found in cartilage tissue, and is highly involved with the control of osteogenesis. Thus, GAGs are distributed and structured in various tissues according to their function, controlling the growth of specific cells.

The present inventors performed basic research into GAGs including heparin/HS which have such diverse functions and especially into their application to medicine, in the process of which they synthesized glycosaminoglycan-functionalized polymers formed by binding the backbones of GAGs to vinyl polymer main chains, and filed a patent application to cover their use as cell culture media and anti-tumor agents (WO 00/59967). This type of functionalization enables the activity of cell growth possessed by GAGs to be efficiently enhanced.

On the other hand, cell-adhesive proteins, collagen among them, which are the main ingredients forming extracellular matrices together with PGs, are commonly used in cell culture substrates and artificial organs for their cell-adhesive properties. For example, various cell types including fibroblasts, endothelial cells and neutrophils have been demonstrated to adhere to matrices consisting only of collagen, where they can grow or migrate. Additionally, this type of adhesion has been shown to depend on the number of cell surface receptors such as members of the integrin family (Myles, J. L. et al., *J. Biomater Sci. Polymer Edn.*, 11:69–86, 2000).

In the field of tissue remodeling which has lately been the focus of increased interest, various attempts have been made to control differentiation/proliferation of various types of cells ex vivo. In general, differentiation gives preference to the expression of functions specific to the cell while inhibiting cell proliferation, and proliferation (dedifferentiation) gives preference to multiplication over function. In the process of tissue regeneration, it is important to maintain a balance between proliferation (dedifferentiation) and the expression of specific functions due to differentiation. Generally, collagen is considered to tend to induce dedifferentiation during in vitro cell cultivation.

SUMMARY OF THE INVENTION

The present inventors performed research on a biomimetic basis, by combining cell-adhesive proteins such as collagen with GAG-functionalized polymers as described above to mimic an environment similar to the extracellular matrix consisting of collagen and PGs, and controlling cell differentiation/proliferation therein. Such attempts to reproduce the extracellular matrix structure using artificial materials have been heretofore unknown. As a result, it was discovered that the above-described GAG-functionalized polymers adhere more strongly to cell-adhesive proteins such as collagen than does naturally occurring heparin, and that heparin-binding growth factors such as FGF-2 and VEGF165 can be effectively immobilized to the collagen substrates to which GAG-functionalized polymers have been adsorbed. Additionally, upon considering that even among GAGs, chondroitin sulfate and hyaluronic add are contained in large amounts in cartilage tissue and are likely to contribute significantly to controlling osteogenesis, it was discovered that osteogenesis can be accelerated by similarly forming functionalized polymers from these and combining the polymers with collagen and the like, thereby achieving the present invention.

Thus, the present invention offers a glycosaminoglycan-functionalized polymer/protein composite comprising a protein carrying a glycosaminoglycan-functionalized polymer obtained by incorporating a carbohydrate chain containing a structure corresponding to at least a portion of a glycosaminoglycan backbone into a vinyl polymer main chain.

The glycosaminoglycan-functionalized polymer/protein composite (hereinafter referred to as "GAG protein composite") of the present invention has a structure analogous to an extracellular matrix consisting of a cell-adhesive protein such as collagen and a proteoglycan (PG), wherein the glycosaminoglycan-functionalized polymer (hereinafter referred to as "GAG polymer") functions at least as well as natural PGs with regard to controlling cell proliferation/differentiation and adhesion of growth factor and cytokines, the composite surface being capable of holding many types of growth factor and cytokines in concentrated form, and able to further accelerate derivation of cartilage tissue and the like. In particular, the heparin/heparan sulfate type GAG polymers can improve the efficiency of control of cell proliferation/differentiation due to the enhanced interaction with growth factor and cytokines, thus accelerating derivation of cartilage tissue and the like.

PREFERRED MODE FOR CARRYING OUT THE INVENTION

Figure 1:
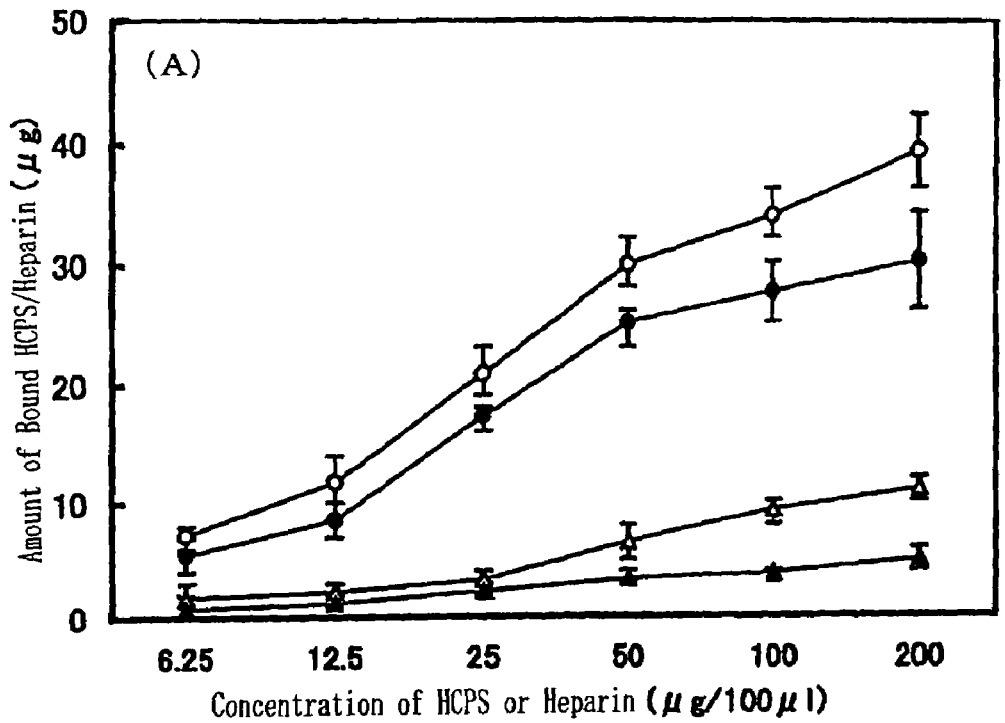
FIG. 1 illustrates graphs showing the binding ability of HCPS and naturally occurring heparin with respect to a collagen-coated 24-well plate (A) and a collagen film (B). The coating was performed overnight at 4° C. using aqueous solutions of the concentrations indicated on the horizontal axis. The amounts of HCPS (○) and heparin (●) left bound after rinsing twice with PBS-BSA, and the amounts of HCSP (△) and heparin (▲) left bound after similarly rinsing with PBS-BSA containing 0.5M NaCl are shown. The data in the drawings represent averages ±SD after three trials.
Figure 1:
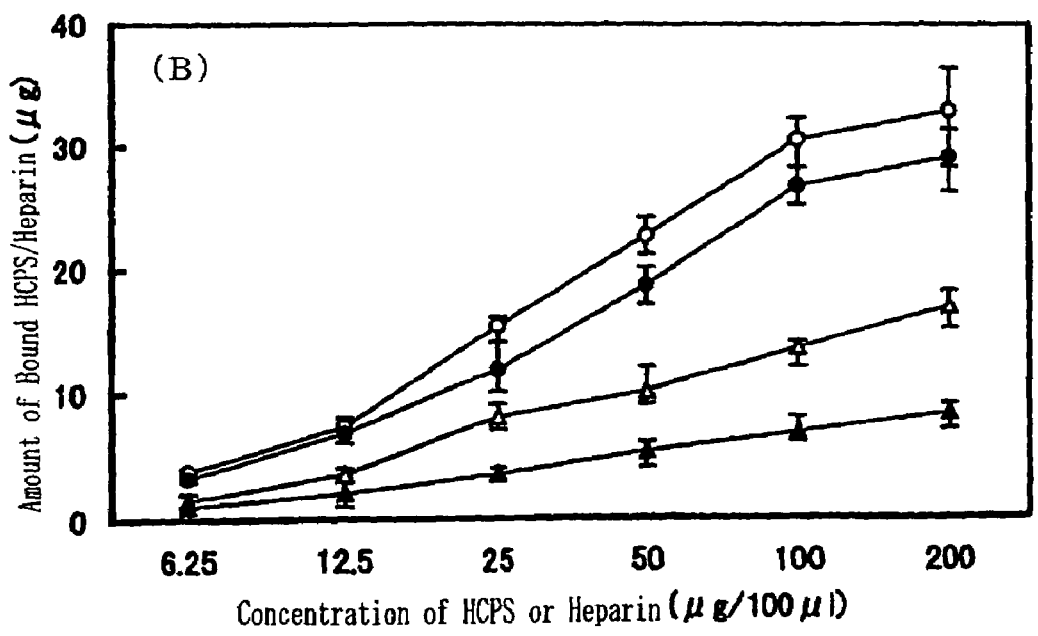

The GAG polymer composites of the present invention are formed by combining a cell-adhesive protein with a glycosaminoglycan-functionalized polymer (GAG polymer) obtained by incorporating a carbohydrate chain containing a structure corresponding to at least a portion of a glycosaminoglycan backbone into a vinyl polymer main chain.

The vinyl polymers used as the GAG polymer main chains in the present invention are composed of polymeric monomers, and may, for example, be homopolymers or copolymers containing monomers selected arbitrarily from among the addition polymerization type, condensation polymerization type, polyaddition type, addition condensation type and ring-opening polymerization type monomers listed in *Kagaku Binran* [Handbook of Chemistry] (pg. 561, Applied Chemistry ed. I, The Chemical Society of Japan, Maruzen, 1986), with no particular restriction thereon. Preferred are monomers of addition polymerization type having at least one unsaturated bond, for example, polymers formed from one or more ethylenes, propylenes, styrenes, vinyl acetates, acrylic acids, methacrylic adds, acrylamides or the like, these being also capable of being optionally substituted.

The GAG polymers of the present invention having a carbohydrate chain with a structure corresponding to at least a portion of the glycosaminoglycan backbone bound to a polymer main chain contains at least one of the units represented by the following general formula (1):

$$—(CWX—CYZ)_n— \qquad (1)$$

In the above formula, W denotes a carbohydrate chain; X, Y and Z denote arbitrary substituent groups including hydrogen atoms or alkyl groups such as methyl or ethyl, acyl groups such as acetyl, alkoxy groups, aryl groups, aralkyl groups, carboxyl groups, amino groups, amido groups and cyano groups; and n denotes the number of repeating units of preferably 2–1000, more preferably 5–500, and even more preferably 10–300.

The carbohydrate chains forming the GAG polymers of the present invention are oligosaccharides or polysaccharides having structures corresponding at least in part to the backbone forming GAGs such as heparin/HS, chondroitin sulfate, dermatan sulfate, keratan sulfate and hyaluronic add, the number of constituent disaccharides being at least 2–50, and more preferable at least 4–25. For example, a carbohydrate chain consisting of at least a pentasaccharide sequence corresponding to the characteristic structural domain held by the 3-O-sulfate group contained in heparin/HS binds specifically to antithrombin III which inhibits blood coagulation, while a carbohydrate chain corresponding to a structural domain of at least a decasaccharide sequence containing 2-O-sulfate groups and 6-O-sulfate groups in abundance will contribute to active expression of FGF-1 and FGF4. On the other hand, not only GAG polymers having sulfate groups known to be crucial to binding with growth factor, but also GAG polymers having a hyaluronic add structure not possessing any sulfate groups are also suitable for use.

If the aforementioned carbohydrate chains possess, for example, N-sulfate groups, then they can be modified by selective desulfation, and may be chemically synthesized or naturally occurring. However, a decomposed carbohydrate chain obtained by chemical decomposition of natural glycosaminoglycans, wherein the decomposed carbohydrate chain binds to a polymer main chain via a functional group formed by the chemical decomposition is preferable for purposes of simplifying the production process.

Examples of naturally occurring GAGs possessing sulfate groups include heparin/HS, chondroitin sulfate (including those having various 4-sulfate/6-sulfate structural ratios such as chondroitin A-E commercially available from Seikagaku Kogyo KK, and those having a disaccharide disulfate structure), dermatan sulfate and keratan sulfate, among which heparin/HS which have many possible patterns of sulfation of the constituent carbohydrates are preferable, but there is no problem with use of other types of GAGs, chondroitin sulfate and dermatan sulfate, for example, being suitable for regeneration of cartilage tissue. Additionally, it is possible to use homopolysaccharides such as cellulose, amylose, laminaran, agarose, carrageenan, inulin, levan, xylan, mannan, chitin, pectin, amylopectin, galactan, triticin, arabinan and colominic acid, or heteropolysaccharides such as glucomannoglycan, galactoglucomannoglycan, guar gum, arabinogalactoglycan, gum arabic, tragacanthic acid and alginic acid into which sulfate groups have been enzymatically or chemicaly incorporated.

The chemical decomposition of naturally occurring glycosaminoglycans can be suitably achieved by using nitrous add or periodic acid to sever the carbohydrate chain bonds in polysaccharides such as those mentioned above under non-physiological conditions outside pH 6.5–8.0, preferably in the acidic and/or alkaline regions of at most pH 5 or at least pH 10, to obtain a fractionated carbohydrate chain. Additionally, it is also possible to obtain fractionated carbohydrate chains by means of selective carbohydrate-reducing enzymes such as heparinase, heparitinase, chondroitinase and keratanase, or in some cases, even by means of chemical decomposition using heat, plasma discharges or radical reactive reagents.

The carbohydrate chains in the GAG polymers of the present invention bind to the polymer main chains by means of covalent bonds. There is no particular restriction on the bonds, which couple functional groups possessed by a polymer main chain and a carbohydrate chain in accordance with the combinations of functional groups thereon, under appropriate reaction conditions and using any type of catalyst. Additionally, while it is possible to bind monomers constituting the polymer main chains with carbohydrate chains to form carbohydrate-carrying monomers, then polymerizing the monomers and to couple carbohydrate chains to pre-polymerized polymers having reactive groups, it is preferable to polymerize carbohydrate-carrying monomers because of the possibility of adjusting the carbohydrate content in a single molecule. Among these, GAG polymers (homopolymers) obtained by introducing fractionated hydrophilic carbohydrate chains into hydrophobic monomer units and polymerizing these have the properties of having a high density of carbohydrate chains in each molecule and readily attaching to hydrophobic resin products even while being water-soluble polymers.

As one possible embodiment, the carbohydrate chains in the GAG polymers of the present invention can be introduced, for example, by means of Schiff bonds through, for example, aldehyde groups and carbonyl groups formed on chemically decomposed GAGs to monomers having amino groups such as vinylbenzylamine. In another embodiment, a method of coupling vinyl monomers and the functional groups of carbohydrate chains using coupling agents having an add chloride group, an N-hydroxysuccinic acid imide ester group or an epoxy group is preferably used. In particular, a method of using aldehyde groups formed on the GAGs by means of chemical decomposition is preferably used for being convenient and allowing for GAG activity to be readily preserved.

These GAG polymers of the present invention contain a plurality of active domains of naturally occurring GAGs in each molecule forming a three-dimensional structure, thereby enhancing the bioactivity of the active domains (cluster effect). With GAG polymers having a heparin/HS structure, for example, the interaction with the various types of cell growth factors and cytokines especially increases, while GAG polymers having a chondroitin sulfate or dermatan sulfate structure will boost the chondrocyte derivation activity. While the number of active domains in a molecule are maximized in homopolymers wherein vinyl monomers incorporating carbohydrate chains are homopolymerized, they can also be formed into copolymers by copolymerization with other monomers not having carbohydrate chains depending on the intended purpose and manner of use, their formulation being within the range of the normal level of technical expertise of those skilled in the art.

On the other hand, the cell-adhesive proteins forming the GAG protein composites of the present invention can be suitably selected from among naturally occurring proteins forming extracellular matrices, these including fibrous proteins such as collagen and elastin, and glycoproteins such as fibronectin, laminin and vitronectin. Collagen, laminin and fibronectin are preferable, and even among these, collagen is particularly suitable for use due to its availability and general applicability to industry.

The GAG protein composites of the present invention are formulated by causing the GAG polymers to be held in a substrate consisting of the cell-adhesive proteins. As described above, the GAG polymers of the present invention have a plurality of hydrophilic (water-soluble) carbohydrate chains bound to a hydrophobic vinyl polymer main chain, so that they are believed to exist in aqueous solutions in a state wherein the polymer main chain constitutes a core which is surrounded by carbohydrate chains, as a result of which the GAG polymer in its complete form is water-soluble. Therefore, by adding an aqueous GAG polymer solution to a collagen substrate or the like, then removing the excess aqueous solution by aspiration or the like if necessary, and letting stand for a certain period of time, it can easily be made to adsorb and immobilize. Depending on the situation, it can then be rinsed with PBS containing bovine serum albumin (BSA-PBS).

The GAG polymers used in the present invention are characterized in that the hydrophobicity of the polymer main chains enables them to attach (adsorb) to hydrophobic resin surfaces, for example, the synthetic resin products such as polystyrene, polycarbonate, polyamide, polysulfone and polyester products which are widely used in medicine. However, quite surprisingly, they were found also to bind very strongly to cell-adhesive protein surfaces such as collagen. In particular, it was experimentally confirmed that heparin/HS type GAG polymers have a binding force stronger than natural heparin molecules. The present inventors believe that this strong binding force is due not only to the simple static adsorption of the GAG polymers, but also to the hydrophobic interaction between the hydrophobic main chain of the GAG polymers and the hydrophobic portions present in the cell-adhesive proteins. There is no particular restriction on the quantity of adsorbing GAG polymers, and this will also depend on the form of the cell-adhesive protein such as collagen (whether film, membrane of a certain thickness or a three-dimensional sponge), but this can be easily adjusted according to the concentration and amount of the aqueous GAG polymer solution used as well as the presence or level of cleansing. For example, when an aqueous GAG polymer solution with a concentration of about 1–1000 μg/100 μl is used, the amount of the GAG polymers such as heparin or the like held per $cm^2$ of the cell-adhesive protein film can be about 1–100 μg. Additionally, if the concentration of the GAG polymer solution is made 10–200 μg/100 μl, then the amount of the immobilized GAG polymer will be about 5–50 μg after rinsing.

The GAG protein composite of the present invention has a form based on the shape of the cell-adhesive protein substantially constituting the substrate, having a structure wherein GAG polymers are held on the surface, or even inside of porous bodies of a three-dimensional shape. The cell-adhesive proteins forming the substrate may be of any form depending on the purpose and manner of use. For example, materials consisting only of cell-adhesive proteins such as collagen can be appropriately molded to form a substrate, or cell-adhesive proteins can be held on surfaces of other materials to form a substrate. Collagen films and collagen sponges consisting substantially of collagen are examples of the former, while dishes, plates, beads and the like whose surfaces have been coated with cell-adhesive proteins such as collagen are examples of the latter. In other words, collagen films with a certain thickness from a flat collagen-coated plate, or a three-dimensional collagen sponge can be used as a substrate to carry GAG polymers on the surfaces thereof, so that variations are possible from almost two-dimensional structures to three-dimensional structures.

The GAG protein composites obtained in this way can be provided as they are as cell culture substrates of various formats. Thus, the present invention also offers a cell culture substrate characterized by containing the above-described GAG protein composites. Such cell culture substrates may comprise dishes, plates, beads or the like provided with the GAG polymer composites of the present invention on their surfaces, or may consist of only the GAG protein composites. GAGs are immobilized to the surfaces of these cell culture substrates at a high density. Consequently, various types of cell growth factors or cytokines can be efficiently adhered, concentrated and held, while also enabling the activity of chondroitin sulfate or the like with a high tissue specificity to be enhanced.

GAGs including heparin/HS are commonly known to bind to various growth factors and cytokines including fibroblast growth factor (FGF), hepatocyte growth factor (HGF), vascular endothelial growth factor (VEGF), heparin-binding epidermal growth factor (HBEGF), platelet-derived growth factor (PDGF), transforming growth factor β (TGF-β), granulocyte macrophage colony stimulating factor (GMCSF), interleukin (IL-1, IL-2, IL-3, IL4, IL-6, IL-7 and IL8), interferon γ and macrophage inflammatory protein 1 (MIP-1). Accordingly, these heparin-binding growth factors and cytokines bind effectively to the surfaces of the GAG protein composites of the present invention. As described in the examples given below, with the GAG protein composite surfaces of the present invention, FGF-1, HGF, HBEGF, TGF-γ, GM-CSF and IL-3 in addition to FGF-2 and VEGF165 were observed to effectively concentrate and attach to HCPS-bound collagen surfaces. That is, the GAG protein composites of the present invention offer exceptional biomaterials for immobilizing and holding various growth factors and cytokines including those with heparin-binding ability.

When using the GAG protein composites of the present invention as cell culture substrates, the above-described growth factors and cytokines may be present in a free state in a system containing the GAG protein composites of the present invention and the subject cells, or may be immobilized to the GAG protein composites. The present inventors discovered that in a system containing both collagen which is a cell-adhesive protein or a GAG protein composite of the present invention and free fibroblast growth factor FGF-2, use of GAG protein composites will promote cell growth of human umbilical vascular endothelial cells or the like with lower concentrations of growth factor than the use of a substrate of only collagen. Furthermore, it was found that while the change in the cell proliferation enhancement effect is slight even when changing the growth factor concentration when a growth factor such as FGF-2 is immobilized to a substrate of only collagen, the cell proliferation is enhanced in accordance with the concentration of the growth factor when growth factor is immobilized to the GAG polymer composite of the present invention, with the results being better than for the case where a substrate of only collagen is used, at any growth factor concentration. Thus, in one embodiment of the GAG protein composite of the present invention, growth factor and cytokines are immobilized to the composites at a high density. The GAG polymer composites of the present embodiment can, as a matter of course, be used as they are as cell-adhesive substrates such as described above.

While there is no particular restriction on the amount of growth factor or cytokines used, when included in a free state in a system, they should be provided in an amount of about 0.01 ng/ml to about 500 ng/ml, preferably about 0.05 ng/ml to about 100 ng/ml, and more preferably about 0.1 ng/ml to about 20 ng/ml, the concentration when immobilizing to a composite being preferably at least about 0.01 ng/ml, preferably at least about 0.1 ng/ml, and more preferably at least about 1 ng/ml. While the amount immobilized to the composites will simply increase depending on the concentrations of growth factor or cytokines used, the immobilization saturation rate can be readily increased in accordance with the shapes and surface areas of the composites.

The present inventors further discovered, surprisingly, that the GAG protein composites of the present invention can enhance cell proliferation and differentiation even in the absence of growth factor. For example, when a heparin-binding growth factor is concentrated to high levels in a GAG protein composite based on growth factor-binding heparin/HS, proliferation of fibroblasts and endothelial cells will be promoted as described above, but even if growth factor is not added, cell proliferation can be well promoted as compared with the case of cultivation on a substrate of only collagen which is a cell-adhesive protein. Furthermore, when cultivating chondrocytes using GAG polymers based on chondroitin sulfate or dermatan sulfate, the chondrocyte proliferation was markedly improved in systems without growth factor over cases where only collagen was used.

That is, like GAG protein composites combining various types of growth factor and cytokines, the GAG protein composites of the present invention not containing growth factor or cytokines are offered as new biological raw materials for controlling cell growth such as proliferation and differentiation in the field of cell and tissue engineering.

Thus, similar to the GAG protein composite combined with various growth factors and cytokines, the GAG protein composites without growth factors and cytokines on the present invention can also provide new materials for cell and tissue engineering which control cell growth including proliferation and differentiation.

These materials can be offered in any form as needed. That is, for example, GAG protein composites having GAG polymers attached to sponge or sheet form collagen substrates are suitable for implantation into the body, which enables artificially constructed PG-like structures to be formed in vivo. In such structures, the growth factors having GAG binding ability become attached, thereby promoting proliferation of cells stimulated by these growth factors. For example, an environment having FGFs adhered and concentrated at high levels results in enhanced differentiation and proliferation of chondrocytes, thereby eventually regenerating the cartilage tissue. As a result, the present invention also offers a material for tissue reconstruction treatments consisting of the above-described GAG protein composites.

While the following examples are given to explain the present invention in further detail, the present invention is by no means restricted to these examples.

EXAMPLE 1

1. Preparation of Heparin-carrying Polystyrene

As a GAG polymer, heparin-carrying polystyrene (HCPS) was prepared by a method described in M. Ishihara et al., *J. Biomed. Mater. Res.*, 50:144–152 (2000). Put simply, heparin (25 g) from porcine intestines was dissolved in 400 ml of a 0.05M sodium acetate buffer (pH 5) containing 0.1M $NaIO_4$, then stirred for three days at 4° C. Next, the remaining $NaIO_4$ was neutralized by adding glycerol (25 ml), after which the reaction mixture was dialyzed and lyophilized. The resulting product (periodic acid-oxidized heparin) was decomposed in an alkaline solution (pH 12) at room temperature for 30 minutes, then dialyzed and lyophilized, after which the decomposed product was recovered as periodic acid-oxidized, alkali-decomposed ($IO_4$-LMW) heparin.

This $IO_4$-LMW-heparin (500 mg) and N-p-vinylbenzylamine (250 mg) were dissolved in 20 ml of 50 mM N,N,N',N',-tetramethyl-ethylenediamine (pH 4.75), after which 1 ml of 0.8 mM $NaCNBH_3$ was added. The reaction mixture was stirred for 24 hours at room temperature, dialyzed and lyophilized to obtain a white powder (heparin-carrying monostyrene). This powder (100 mg) and 2 mg of potassium sulfate peroxide were dissolved into 1 ml of distilled water, then polymerized for 24 hours at 60° C. under dry $N_2$. The reaction solution was introduced into an excess amount of ethanol, to obtain a polymer as a precipitant. Water-soluble impurities were removed from the precipitant by ultrafiltration, and after lyophilization, HCPS was obtained in the form of a white powder.

2. Binding of HCPS to Collagen-Coated Culture Plate and Collagen Film 96-well and 24-well suspension culture plates (Sumitomo Bakelite) were coated by leaving overnight at 4° C. in 0.03 wt % of I-type collagen (Kouken) in respectively 50 and 200 µl of acidic solution (pH 3). The remaining collagen solution was removed from the wells by aspiration, and the plate was rinsed twice with a phosphate buffer (PBS). Next, each collagen-coated plate was coated overnight at 4° C. with 50 µl (96-well plate) and 200 µl (24-well plate) of aqueous HCPS solution (e.g. 0.1 wt %). Next, the remaining HCPS solution was removed from the wells by aspiration, and the plates were rinsed twice with a 0.5M NaCl solution in PBS containing 1 wt % of bovine serum albumin (BSA-PBS), and twice with BSA-PBS. The amount of HCPS immobilized to the collagen-coated plate was estimated using a carbazole assay (T. Bitter et al., *Anal. Biochem.*, 4:330–34 (1962)).

Additionally, the collagen film (64 $mm^2$, Kouken) in the 24-well tissue culture plate was also similarly coated overnight at 4° C. with 100 µl of HCPS. The HCPS-bound collagen film was then rinsed twice with a 0.5M NaCl solution in BSA-PBS, and twice with BSA-PBS. The amount of HCPS immobilize to the collagen film was estimated using a carbazole assay.

Upon binding HCPS to collagen-coated plates and collagen films using HCPS solutions of various concentrations according to the above-given methods, the amount of HCPS bound to the collagen increased with higher HCPS concentrations, but eventually reached an equilibrium (FIG. 1). The amount of HCPS bound to the collagen did not change even after incubation for 3 days at 37° C. (not shown in the data). On the other hand, the naturally occurring heparin molecules used as a control (interactions with various types of collagen are known) bound to collagen-coated plates and collagen films, but the amount of bound heparin was less than that of HCPS (FIG. 1). Furthermore, much of the bound heparin was lost upon rinsing with a 0.5 mM NaCl solution in PBS-BSA.

These results suggest that the strong binding force of the HCPS to the collagen surface is due not only to specific binding of heparin chains to the collagen, but also depends on matching of the three-dimensional structure between the HCPS and the collagen. In general, if a 100 µg/100 µl HCPS aqueous solution is used to prepare an HCPS-binding collagen film, about 10–20 µg of heparin molecules are estimated to be immobilized per $cm^2$ of the collagen surface after rinsing. In this way, the GAG protein composites of the present example were formed.

3. Holding of Growth Factor by GAG Protein Composites

Various concentrations of FGF-2 and VEGF165 in 100 µl of BSA-PBS were added to GAG protein composites (collagen-coated 96-well plate and collagen film with bound HCPS) prepared as described above, then incubated overnight at 4° C. The plates and collagen films were rinsed four times with BSA-PBS, following which 100 µl of anti-FGF-2 or anti-VEGF165 (R&D Systems) diluted to 1:500 with BSA-PBS were added and rocked gently for 1 hour at room temperature. Next, the plates or collagen films were rinsed four times with BSA-PBS, after which 100 µl of anti-IgG (horseradish peroxidase) complex diluted to 1:1000 with BSA-PBS were added and the result further mixed for 1 hour. Next, the plates and collagen films were rinsed four times with BSA-PBS, and 100 µl of horseradish peroxidase substrate solution (Nippon Bio-Rad Lab.) were added, and the result mixed for 1 hour at room temperature to generate color. The OD of each well was read at 414 nm using an immuno mini plate reader (Nunc InterMed).

Figure 2:
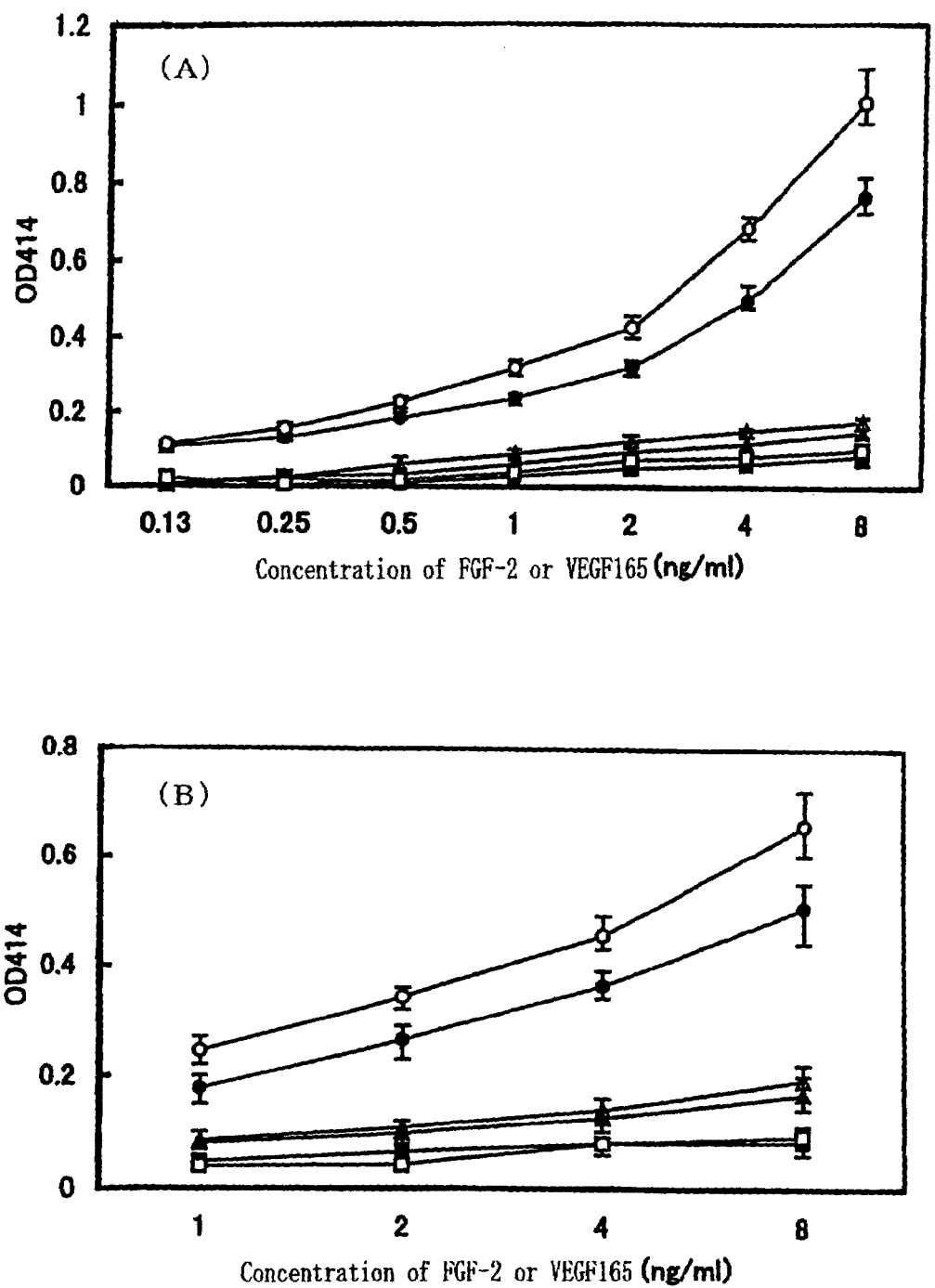
FIG. 2 illustrates graphs showing the immobilization of growth factor (VEGF165 and FGF-2) on a collagen-coated plate (A) and a collagen film (B) with and without HCPS. 100 ml of an aqueous growth factor solution of the concentrations indicated on the horizontal axis were added to each substrate. The immobilization of VEGF165 (○) and FGF-2 (●) to an HCPS-carrying collagen-coated plate or collagen film, VEGF165 (△) and FGF-2 (▲) to a natural heparin-treated collagen-coated plate or collagen film, and VEGF165 (□) and FGF-2 (■) to a collagen-coated plate or collagen film are shown in comparison. The data in the drawings represent averages ±SD after three trials.

The binding abilities of FGF-2 and VEGF165 which are growth factors for stimulating proliferation of the endothelial cells and fibroblasts, specifically binding to heparin, were tested by common ELISA procedures in accordance with the above. Both FGF-2 and VEGF165 were found to attach to GAG protein composites depending on concentration (FIG. 2). The amounts of the attached FGF-2 and VEGF165 did not change even after incubation for 3 days at 37° C. On the other hand, the amounts of these two growth factors binding to collagen only and collagen treated with natural heparin as controls were significantly lower than the amounts binding to the GAG protein composites.

4. Cell Cultivation and Cell-Adhesion Assay

Human umbilical vascular endothelial cells (HUVECs) and human skin fibroblasts were purchased from Takara Biochemical. The cells used in these experiments were from the fourth to eighth passages. The HUVECs were cultivated in 199 culture medium (Life Technology Oriental) to which were added 10% immobilized fetal bovine serum, (antibiotics (100 U/ml penicillin and 100 μl/ml streptomycin) and 10 ng/ml of human recombinant FGF-2 (hrFGF-2, R&D Systems). The fibroblasts were cultivated in DMEM (Life Technology Oriental) to which 10% thermally inactivated FBS and antibiotics (same as above) were added.

In performing the cell-adhesive assay, the cells were freed from the culture dish by treating with trypsin-EDTA solution (Sigma Aldrich), then suspended in each culture medium at a density of $25 \times 10^4$ cells/ml. The cell suspension solutions (0.5 ml for the plates and 0.3 ml for the films) were added to a plurality of collagen-coated 24-well plates and collagen films (GAG protein composites and control products), then incubated for a predetermined period of time. Next, each coated well and collagen film was rinsed three times with PBS. The cells bound to the coated wells and collagen films were freed by treating with a trypsin-EDTA solution. The number of freed cells was counted with a hemocyte meter (Sigma Aldrich).

Figure 3:
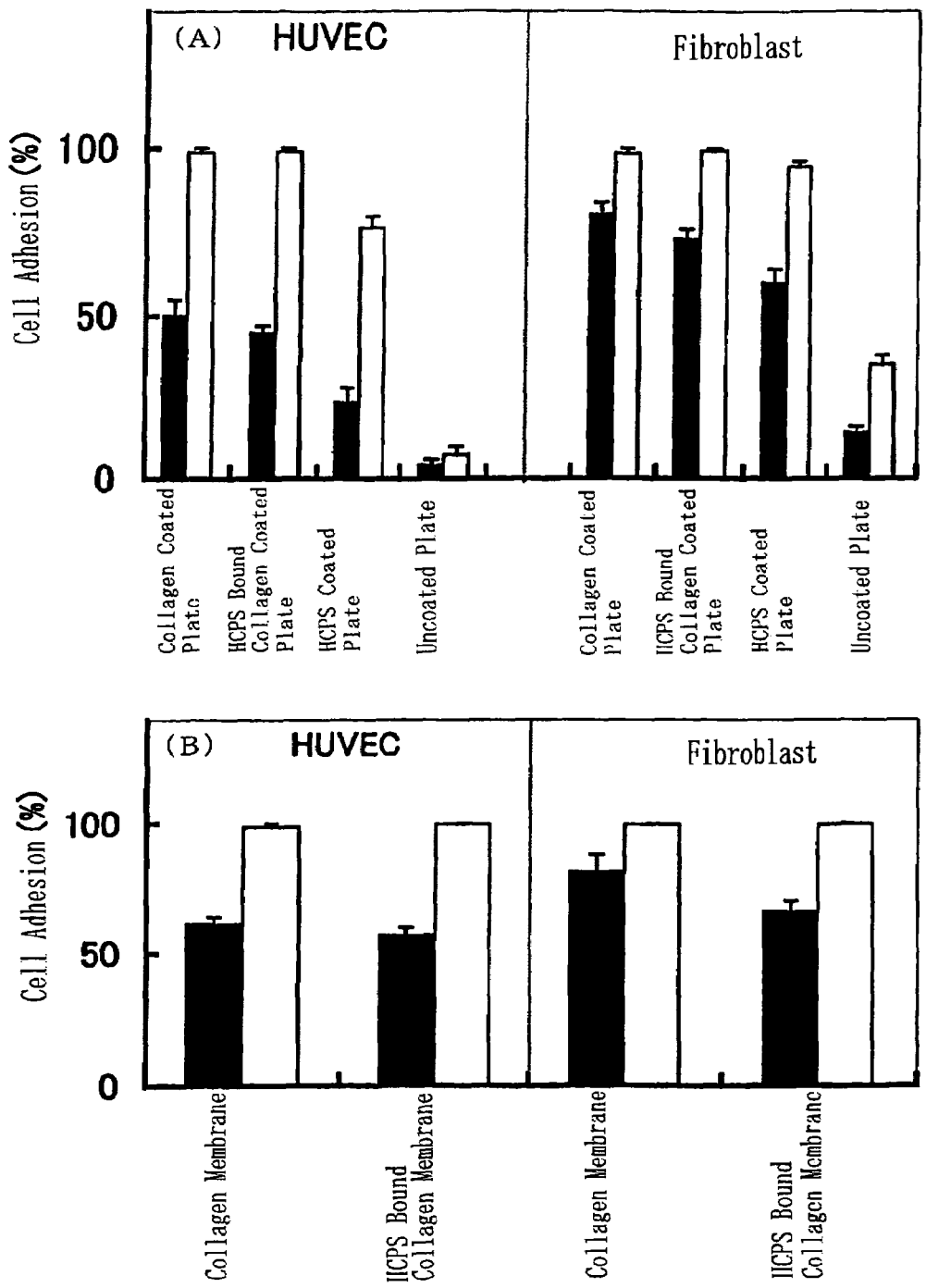
FIG. 3 illustrates graphs indicating the adhesion of HUVECs and fibroblasts to a collagen-coated plate (A) and collagen film (B) with and without HCPS. As controls, the results for a plate coated with only HCPS and an uncoated plate are also shown (A). The values represent those measured after incubation for 1 hour (black bars) and 3 hours (white bars) at 37° C. The data in the drawings represent averages ±SD after three trials.

The results of the above-described cell-adhesion assays are shown in FIG. 3. The GAG protein composite- and collagen-coated plates as well as the collagen films of the present invention exhibited similar adhesive behavior after 1 and 3 hours for both cell types, but the uncoated plates had very low adhesion for both cell types. On the other hand, while the plates coated with only HCPS also exhibited good adhesion for both cell types, it was less than for the collagen substrates (regardless of the presence or absence of HCPS immobilization). That is, while HCPS promotes adhesion of both types of cells, initial adhesion of HUVEC and fibroblasts was found to have a preference for interaction with the collagen substrates.

5. Cell Proliferation Assay (1) When Using Free Growth Factor

In a HUVEC proliferation assay, a predetermined concentration of either FGF-2 or VEGF165 in a 199 medium supplemented with 10% inactivated FBS and an antibiotic were inoculated at an initial density of 6,000 cells per well on a 96-well coated plate or (on a 24-well culture plate) 15,000 cells per collagen film, then cultivated for 3 days. After incubation, the used culture medium was removed, and a fresh culture medium containing 10 μl of WST-1 reagent (Cell Counting Kit, Dojindo) was added to each well. Next, after one hour of incubation, an immuno plate reader was used to read the OD at 450 nm.

In the fibroblast proliferation assay, a predetermined concentration of FGF-2 in a DMEM medium supplemented with 1% inactivated FBS and an antibiotic were inoculated at an initial density of 3,000 cells per well on a 96-well coated plate or 7,000 cells per collagen film. The cells were cultivated for 4 days, and after incubation, the OD of each well or film was measured as described above.

Figure 4:
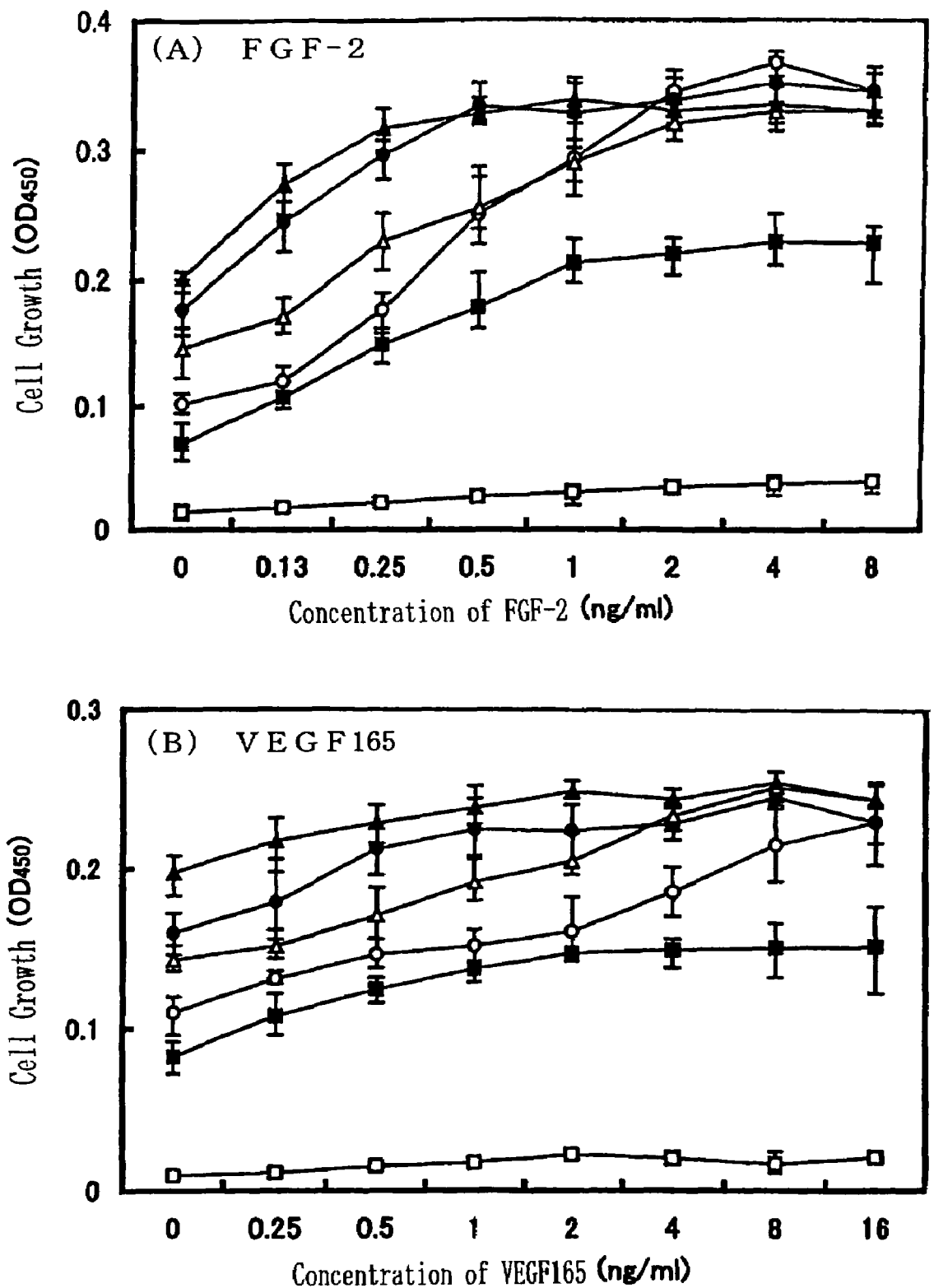
FIG. 4 illustrates graphs showing the effects of carrying HCPS on HUVEC proliferation in a system where free FGF-2 (A) or VEGF165 (B) is present. The HUVECs were inoculated onto an HCPS-carrying collagen-coated plate (●), a collagen-coated plate (○), an HCPS-carrying collagen film (▲), a collagen film (△), a plate coated with only HCPS (■) and an untreated plate (□). The culture media were provided with FGF-2 (A) or VEGF165 (B) at the concentrations shown on the horizontal axis and cultivated for 3 days. The data in the drawings represent averages ±SD after three trials.
Figure 6:
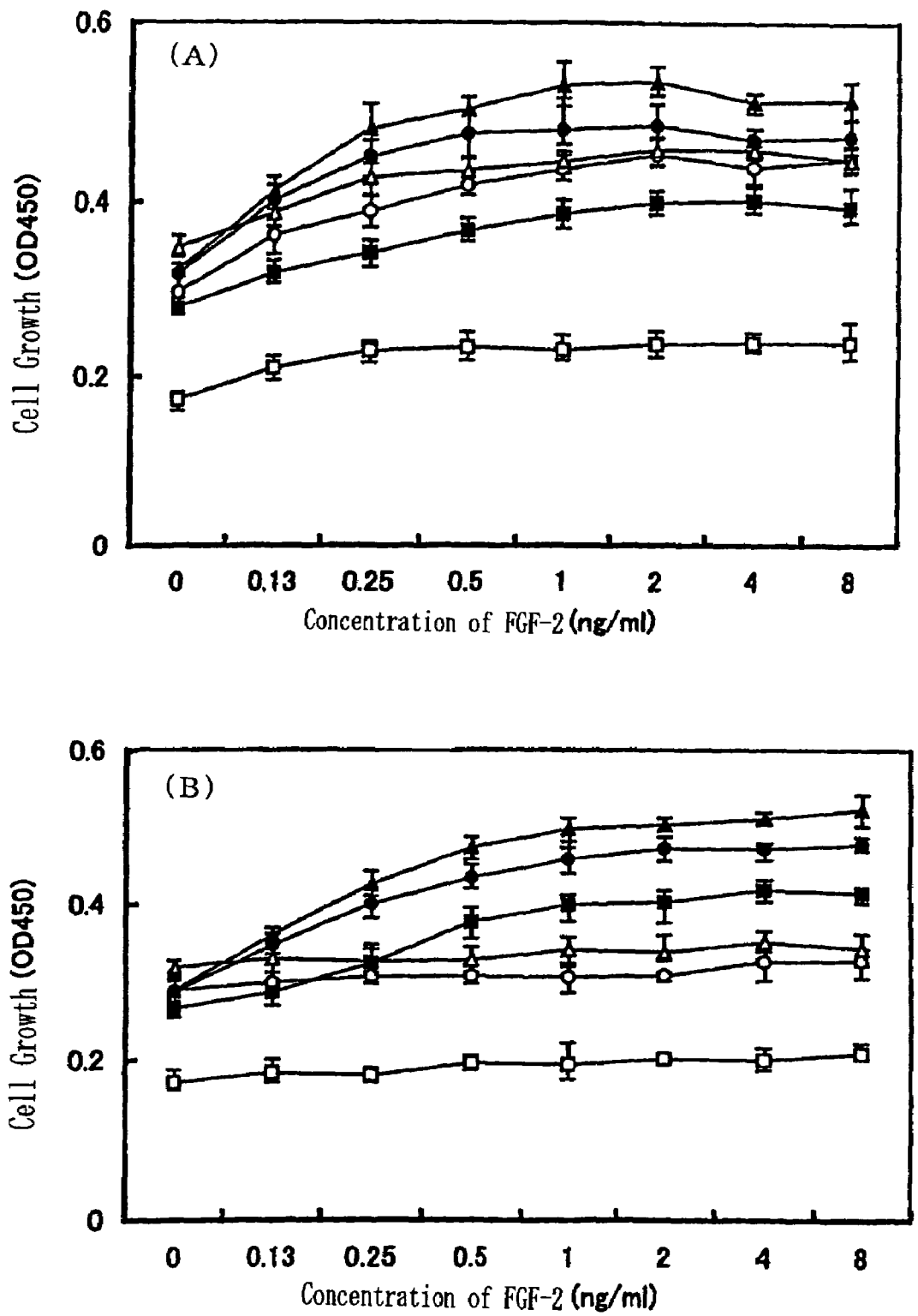
FIG. 6 illustrates graphs showing the effects of carrying HCPS on fibroblast proliferation in a system where free FGF-2 (A) or VEGF165 (B) is present. The fibroblasts were cultivated for 4 days in culture media comprising an HCPS-carrying collagen-coated plate (●), a collagen-coated plate (○), an HCPS-carrying collagen film (▲), a collagen film (△), a plate coated with only HCPS (■) and an untreated plate (□) containing FGF-2 at the indicated concentrations (A), or the above culture media containing growth factor after treating to immobilize FGF-2 at the indicated concentrations. The data in the drawings represent averages ±SD after three trials.

The proliferation of HUVEC for the cases where FGF-2 or VEGF165 are present in the culture medium (respectively FIGS. 4A and B) and of fibroblast cells when FGF-2 is present (FIG. 6A) are shown as functions of the concentration of the various growth factors. Aside from the GAG protein composites of the present invention, tests were performed for cases where only HCPS was coated onto a collagen-coated plate, a collagen film and an uncoated (collagen-free) plate as controls. As a result, the presence of HCPS was found to considerably enhance the growth of HUVECs in the absence of FGF-2 and VEGF165 (FIG. 4). Furthermore, FGF-2 was found to be effective for stimulating HUVEC proliferation depending on concentration in all substrates other than uncoated plates. In particular, HUVEC proliferation was significantly stimulated in low-concentrations of FGF-2 (0.13, 0.25, 0.5 ng/ml) in a GAG protein composite (plate and film). Similarly, fibroblast proliferation was also stimulated in GAG protein composites (FIG. 6A). While VEGF165 does not have more marked effects than FGF-2 for stimulating HUVEC proliferation, stimulation comparable to that of the mitogen activity of VEGF165 was observed at low concentrations.

(2) When Immobilizing Growth Factor

HUVEC in a 199 medium was inoculated onto a GAG protein composite (plate and film) with pre-immobilized FGF-2 and VEGF. The cells were cultivated for 3 days without growth factor in the 199 medium, and the OD was measured as described above. Furthermore, human skin fibroblasts in DMEM were inoculated onto a GAG protein composite (plate and film) with pre-immobilized FGF-2. The OD was measured after cultivating the cells in an FGF-2 free DMEM for 4 days.

Figure 5:
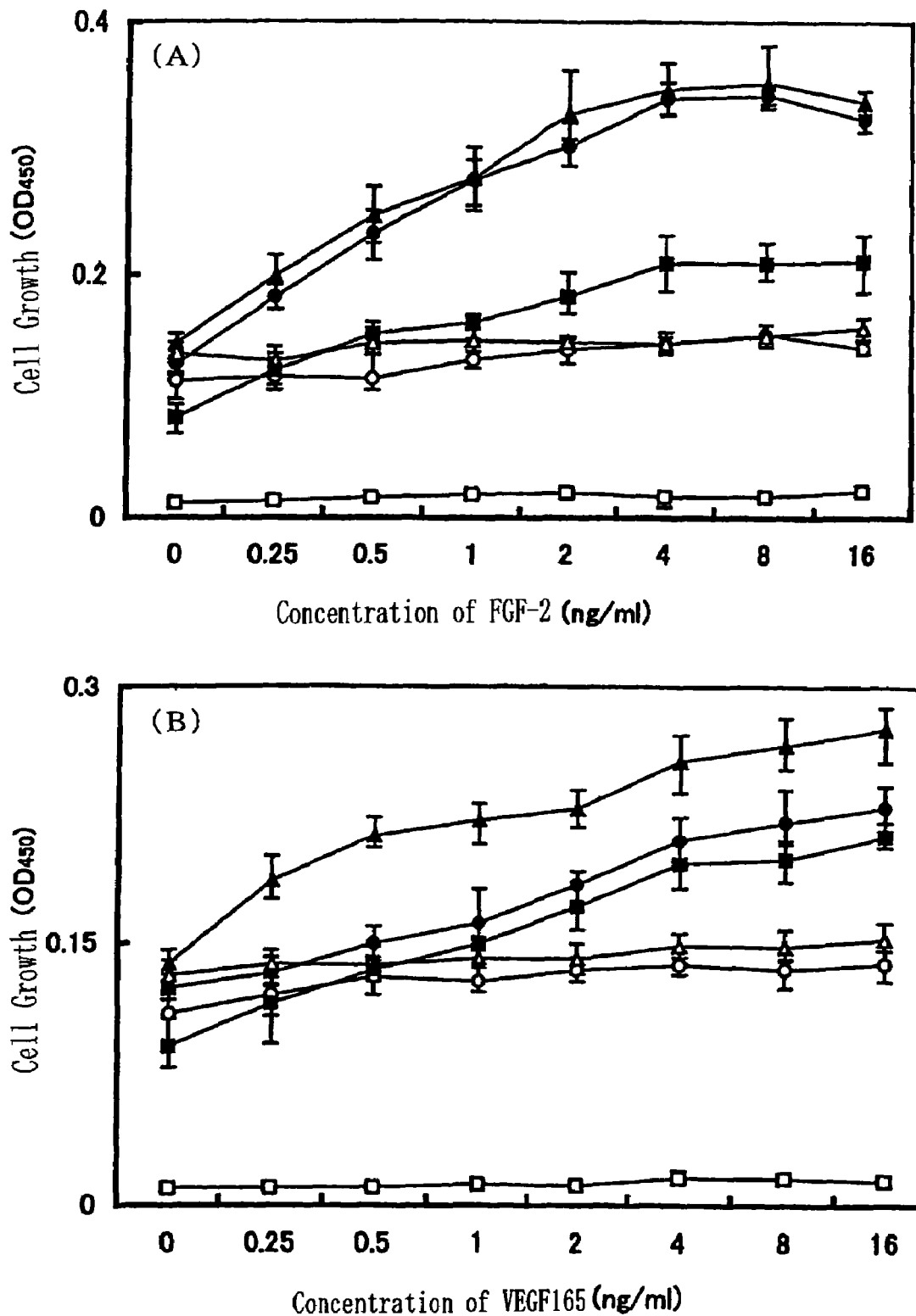
FIG. 5 illustrates graphs showing the effects of carrying HCPS on HUVEC proliferation in a system with immobilized FGF-2 (A) or VEGF165 (B). The HUVECs were cultivated for 3 days in a culture medium not containing growth factor, after treating an HCPS-carrying collagen-coated plate (●), a collagen-coated plate (○), an HCPS-carrying collagen film (▲), a collagen film (△), a plate coated with only HCPS (■) and an untreated plate (□) with FGF-2 (A) or VEGF165 (B) at the concentrations shown on the horizontal axis. The data in the drawings represent averages ±SD after three trials.

The FGF-2 and VEGF165 were immobilized as described above. HUVECs were cultivated in a 199 culture medium (not containing growth factor) on a GAG protein composite (coated plate and film) with immobilized FGF-2 (FIG. 5A) or VEGF165 (FIG. 5B). While HUVEC proliferation was stimulated depending on the concentration of the pre-immobilized FGF-2 and VEGF165 in the GAG protein composite (plate and film), the HUVEC proliferation in collagen-coated plates and collagen films (not carrying HCPS) did not change according to the concentration of pre-immobilized growth factor. Similarly, the growth of fibroblasts was also promoted depending on concentration of the FGF-2 pre-immobilized to the GAG protein composite (FIG. 6B). That is, the GAG protein composite (HCPS-bound collagen substrate) of the present invention offered an exceptional substrate capable of holding a heparin-binding growth factor and stimulating fibroblast proliferation.

EXAMPLE 2

GAG protein composites were prepared using HCPS in a manner similar to Example 1, after which it was observed that other growth factors such as HGF, HBEGF, TGF-γ, GM-CSF and IL-3 were also effectively immobilized.

EXAMPLE 3

1. Preparation of Chondroitin Sulfate-Carrying Polystyrene (PV-CoC)

Chondroitin sulfate-carrying polystyrene was prepared as a GAG polymer in the same manner as in Example 1 but for replacing the heparin with chondroitin sulfate C.

2. Chondrocyte Adhesion Assay

Figure 7:
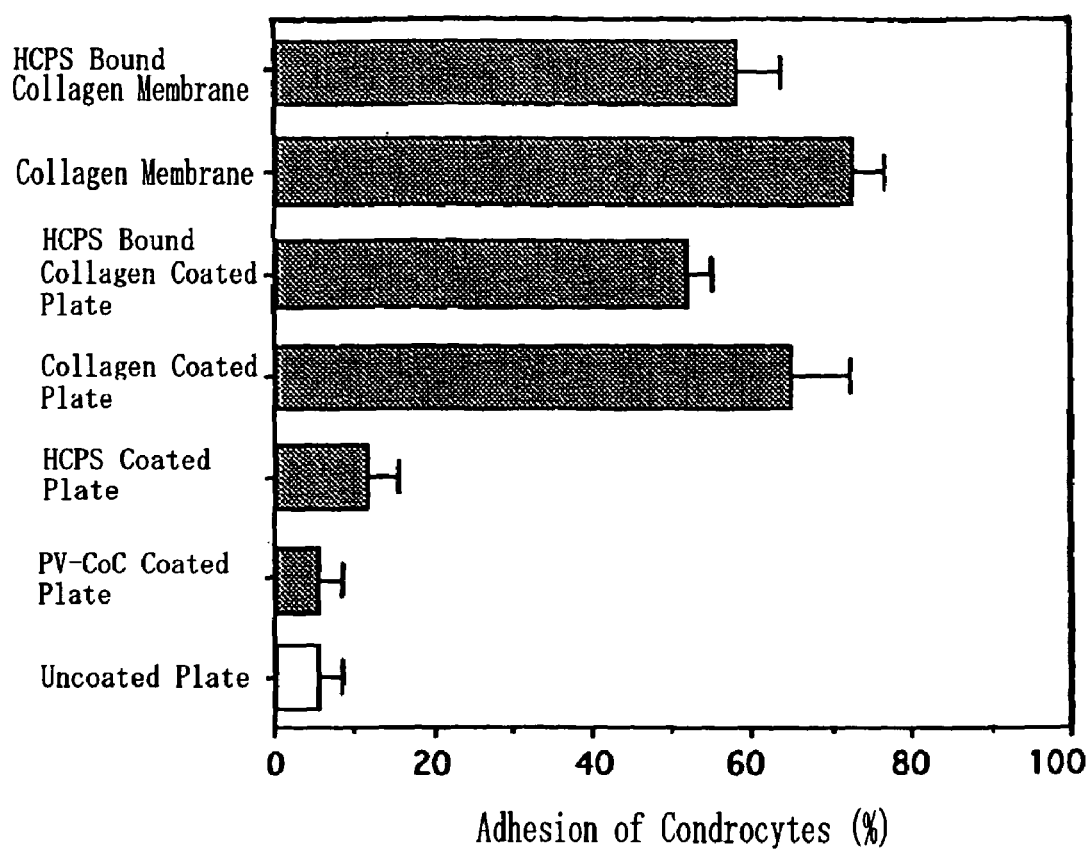
FIG. 7 illustrates a graph showing the adhesion of chondrocytes to collagen-coated plates or collagen films with and without GAG polymers (HCPS or PV-CoC).

A cell adhesion assay was performed on chondrocytes (rabbit) in the same manner as for the endothelial cells and fibroblasts in Example 1. As the substrates, an uncoated plate, a plate coated with only PV-CoC, HCPS or collagen, a collagen film, and GAG protein composites with HCPS immobilized onto a collagen-coated plate or collagen film were used. The results are shown in FIG. 7. As seen in FIG. 7, in the case of chondrocytes, they adhere best to collagen (coated plate and film) which is a cell-adhesive protein, but GAG protein composites with immobilized PV-CoC were found also to have almost the same adhesiveness as the collagen substrate with immobilized HCPS as in Example 1. However, only low adhesion was exhibited in substrates not containing collagen. That is, even in the initial adhesion of chondrocytes, PV-CoC was found to have a preference for interaction with collagen without inhibiting adhesion of the cells to collagen as with HCPS.

3. Chondrocyte Proliferation Assay.

GAG protein composites were prepared using honeycomb-structured collagen sponges (Kouken) as substrates with HCPS or PV-CoC which are GAG polymers immobilized to the surfaces thereof. Growth factors FGF-2 or TGF-β1 were immobilized to these GAG protein composites and collagen sponges, and proliferation assays were performed on chondrocytes thereon. HCPS coating was performed overnight using a 0.1% aqueous solution as described above, and PV-CoC coating was also performed in accordance therewith. Next, FGF-2 or TGF-β1 were coated overnight onto the resulting GAG protein composites or collagen sponges, which were then rinsed for 1 hour with 0.5M NaCl/PBS. After adding a chondrocyte suspension to the culture medium and incubating for 4 days, the proliferation of the chondrocytes was measured. The results are shown in the following Table 1. In Table 1, the proliferation is indicated as a ratio when taking the proliferation in the case where a collagen sponge without immobilization of GAG polymers (control) is used as 1.

TABLE 1

| GAG Polymer | Amt. FGF (ng/ml) | | | Amt. TGF (ng/ml) | | |
|---|---|---|---|---|---|---|
| | 0 | 0.4 | 2.0 | 0 | 0.8 | 4.0 |
| None (control) | 1.00 | 1.10 | 1.30 | 1.00 | 0.96 | 0.94 |
| PV-CoC | 1.33 | 1.44 | 1.51 | 1.33 | 0.92 | 0.82 |
| HCPS | 1.12 | 1.28 | 1.47 | 1.12 | 0.92 | 0.88 |

What deserves attention in Table 1 is the case where no growth factor is added (added amount=0), in which case the chondrocyte proliferation was improved by about 30% over the case where collagen alone is used, for GAG protein composites based on GAG polymers having a chondroitin sulfate structure. This value is greater than the proliferation enhancement effect of HCPS that has a growth factor-binding heparin/HS structure.

Additionally, when growth factor is present, proliferation increases as a function of the FGF concentration while retaining a chondrocyte-like morphology in the case of FGF which enhances cell expansion, while the proliferation slightly decreases while retaining a large cell morphology due to the presence of TGF in the case of TGF which enhances cell differentiation and ECM synthesis, thus enabling cell organization to progress without any problems. Additionally, with only collagen as a control, the fibroblast-like morphology was retained.

When using heparin or chondroitin sulfate which consist of smaller molecules, these are almost all carried away in the rinsing stage, thus allowing only for results on a par with uncoated collagen sponges.

The invention claimed is:

1. A composite of a glycosaminoglycan-functionalized polymer and a cell-adhesion protein comprising a protein carrying a glycosaminoglycan-functionalized polymer obtained by incorporating a carbohydrate chain containing a structure corresponding to at least a portion of a glycosaminoglycan backbone into a hydrophobic vinyl polymer main chain.

2. A composite as recited in claim 1, wherein said cell-adhesion protein is collagen.

3. A composite as recited in claim 1, wherein said glycosaminoglycan-functionalized polymer is represented by the following general formula (1):

—(CWX—CYZ)$_n$—    (1), where W denotes a carbohydrate chain; X, Y and Z denote arbitrary substituent groups including hydrogen atoms; and n denotes the number of repeating units of at least 1.

4. A composite as recited in claim 1, wherein said carbohydrate chain is heparin/heparin sulfate; chondroitin sulfate; dermatan sulfate, or partially desulfated modifications thereof.

5. A composite as recited in claim 1, wherein a growth factor or a cytokine is further immobilized via said glycosaminoglycan-functionalized polymer.

6. A cell culture substrate comprising a composite as recited in any one of claims 1–5.

7. A material for tissue reconstruction treatments comprising a composite as recited in any one of claims 1–5.

* * * * *